US00PP11769P2

(12) United States Plant Patent
Proud

(10) Patent No.: US PP11,769 P2
(45) Date of Patent: Feb. 6, 2001

(54) PEACH TREE NAMED 'CROFT'

(76) Inventor: Margaret J. Proud, Avalon 26715, SE. 168th St., Issaquah, WA (US) 98027-8215

( * ) Notice: Under 35 U.S.C. 154(b), the term of this patent shall be extended for 0 days.

(21) Appl. No.: 09/185,333

(22) Filed: Nov. 2, 1998

(51) Int. Cl.[7] ..... A01H 5/00
(52) U.S. Cl. ..... Plt./197
(58) Field of Search ..... Plt./197, 198

(56) References Cited

U.S. PATENT DOCUMENTS

P.P. 2,343 * 1/1964 Montgomery ..... Plt./197

* cited by examiner

*Primary Examiner*—Howard J. Locker
(74) *Attorney, Agent, or Firm*—Klarquist Sparkman Campbell Leigh & Whinston, LLP

(57) ABSTRACT

The 'Croft' peach is characterized by its production of early to mid-season ripening peaches that are semi-freestone, with yellow flesh, medium to dark red skin coloration, and good peach flavor that is at least comparable to that of other varieties maturing in its season. The dominant characteristic of the variety is its high resistance to peach leaf curl, *Taphrina deformans* (Berk.).

5 Drawing Sheets

BACKGROUND OF THE NEW VARIETY

The present invention relates to a new and distinct variety of peach tree (*Prunus persica*, Batsch.) named 'Croft'. My new peach tree produces semi-freestone fruit which matures about the same time as fruit from 'Early Redhaven' (U.S. Plant Pat. No. 2,343) peach trees, in middle to late July in Wenatchee, Wash., and has outstanding resistance to peach leaf curl disease.

In 1978, the inventor moved onto the property on Tiger Mountain, about 30 miles east of Seattle, Wash. A few years later, some peach seeds germinated in the compost pile located in a cultivated area and one of them exhibited no leaf curl symptoms, while others either succumbed to the disease or were severely infected every year.

The original tree, plagued annually by deer and bears, continues to grow, virtually free of leaf curl, and to produce good quality fruit every year. The climate in this area is very conducive to leaf curl disease, with an average of about sixty inches of rainfall annually, much of it during the winter and spring period when leaf curl commonly attacks peaches and nectarines.

In 1986, after observing that the tree appeared for several years to be free of leaf curl and that the fruit appeared to be of high quality, the inventor contacted Washington State University's Northwestern Washington Research and Extension Unit at Mount Vernon, Wash., requesting an evaluation of this seedling variety. At the inventor's request and direction, the new variety was grafted at that location in 1990 onto seedling peach trees ('Lovell' variety) and has been evaluated there annually since that time. Third generation grafted trees produced asexually at that location in 1996 are presently being evaluated in replicated plots.

In addition, a single tree was grafted in August 1995 for observation at the home of Dr. R. A. Norton, retired director of the WSU research facility in Mount Vernon, Wash. The home is located in East Wenatchee, Wash. East Wenatchee is characterized by a high desert type arid climate (about ten inches of annual rainfall, cold winters and hot summers). Many fruit orchards exist in the Wenatchee, Wash. area. This tree fruited heavily in 1997–2000 with excellent quality peaches and no leaf curl despite the fact that no fungicide was applied to the trees. This resistance exceeds that of any so-called "leaf curl resistant" variety grown in the area, including 'Frost' peach, which is the most common leaf curl resistant variety currently being grown.

The leaves of my new variety lack glands. This is in contrast to leaf curl susceptible peach varieties, including 'Early Redhaven,' with various types of glands. This resistance exceeds that of any so-call "leaf curl resistance" variety grown in the area, including 'Frost' peach (unpatented), which is the most common leaf curl resistant variety currently being grown.

The fruit produced on these second and third generation trees, which were produced by grafting from the original tree, in both western Washington (Mount Vernon) and central Washington (East Wenatchee) were in all respects identical to those on the original tree at Tiger Mountain. Thus, we have confirmed that the new variety reproduces true through asexual means (grafting) at two locations.

DETAILED DESCRIPTION

Figure 1:
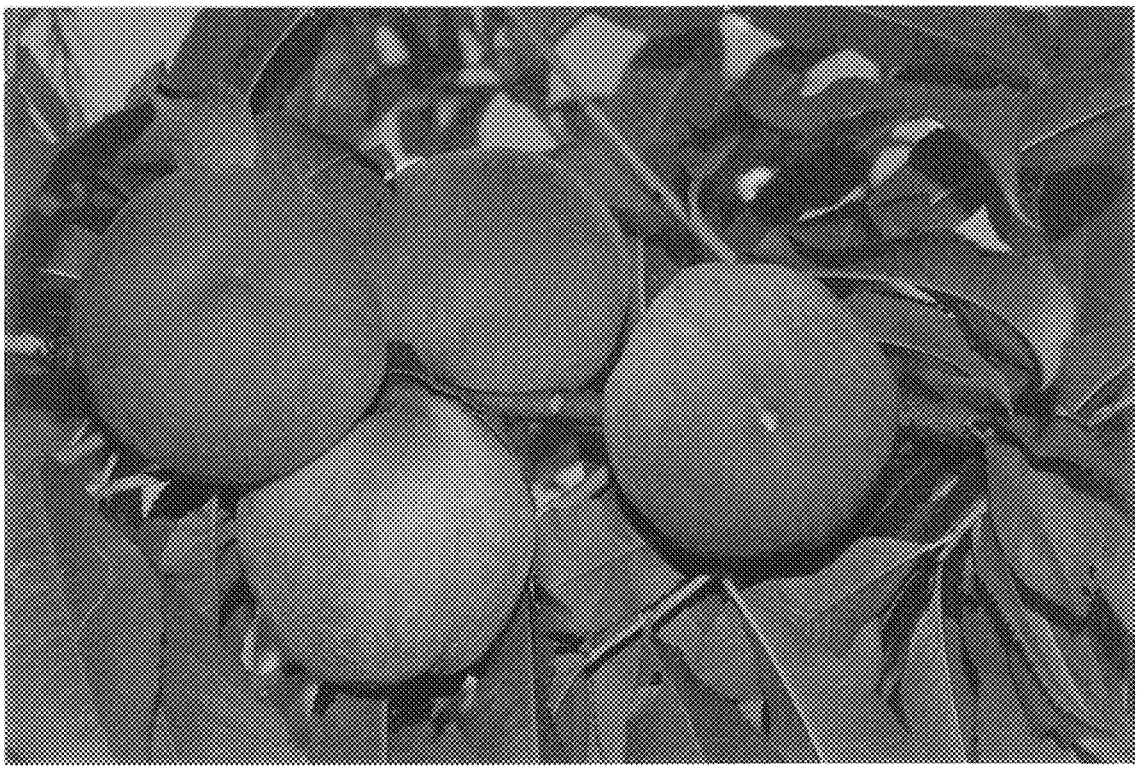
FIG. 1 is a photograph of fruit and foliage of the "Croft" variety of peach tree.
Figure 2:
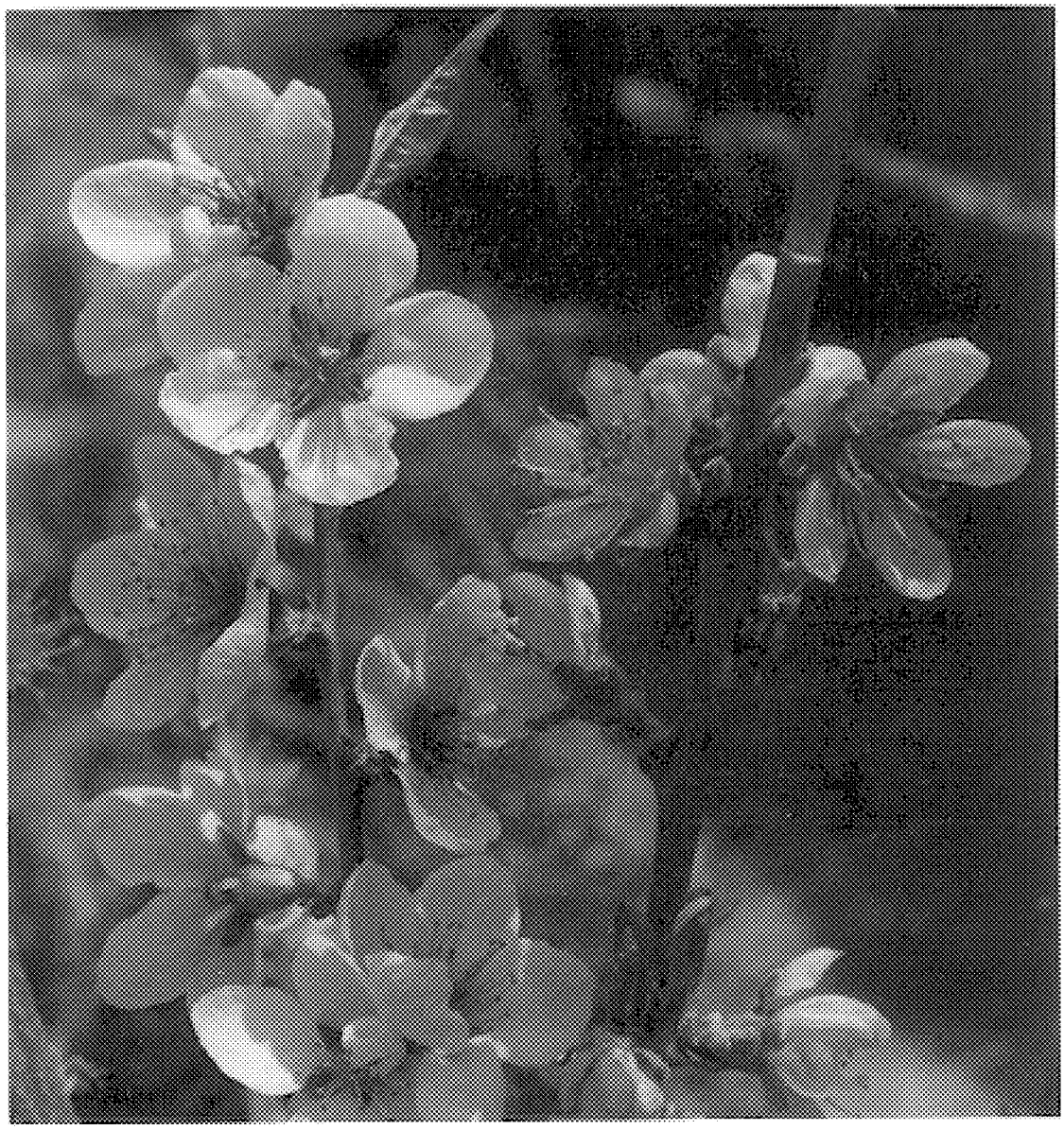
FIG. 2 is a photograph of blossoms of my 'Croft' variety of peach tree (right) compared to a showy type of peach blossom ('Sunhigh' variety) (left).
Figure 3:
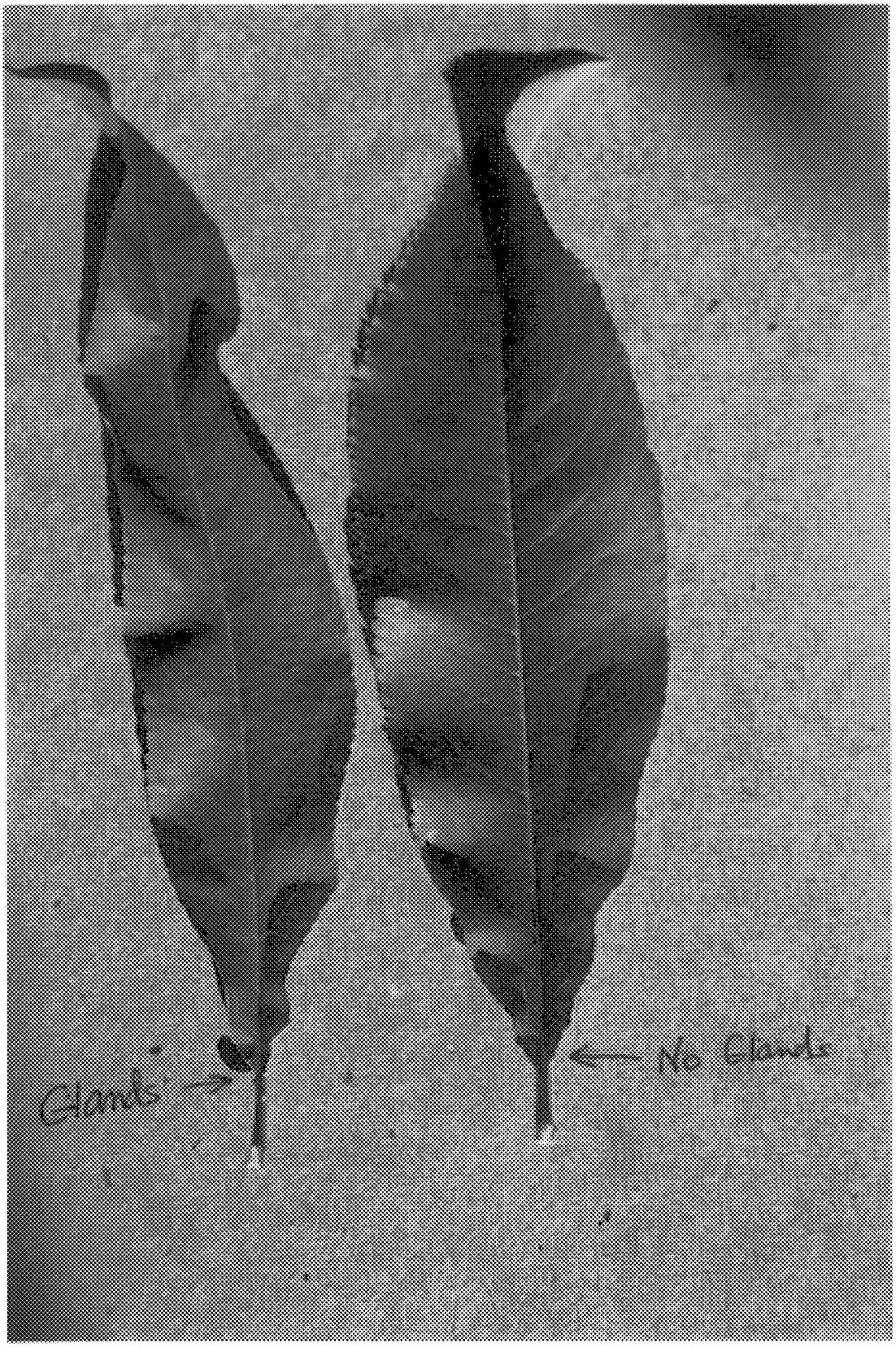
FIG. 3 is a photograph of a typical leaf of my 'Croft' variety (right) showing absence of glands, as compared with a typical leaf of 'Early Redhaven' (left) with glands.
Figure 4:
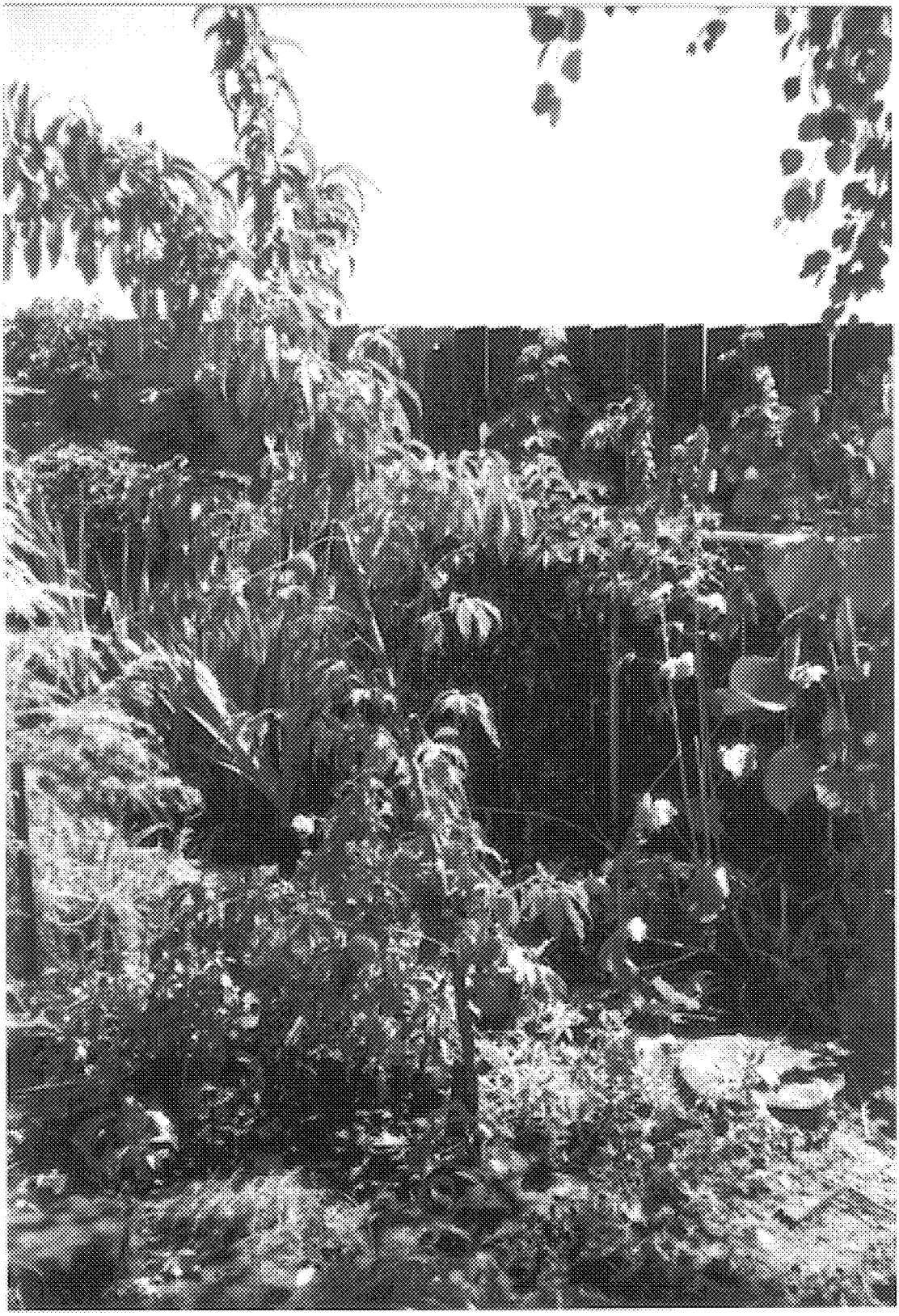
FIG. 4 is a photograph of a three-year old tree of my 'Croft' variety (third generation) growing in East Wenatchee, Wash.
Figure 5:
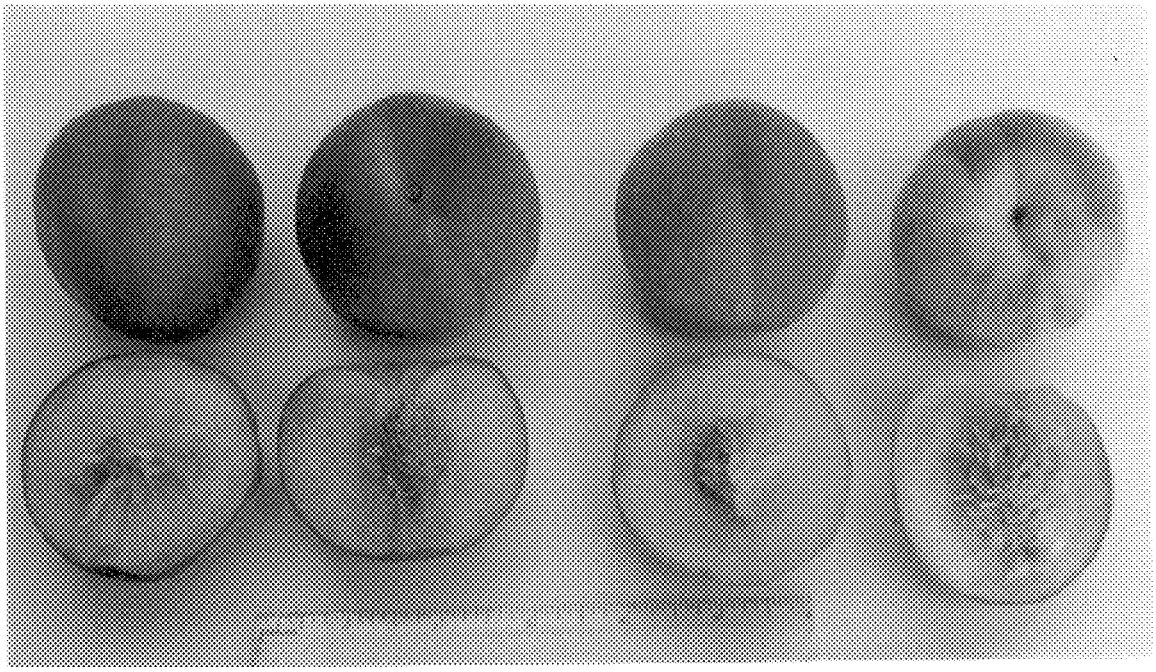
FIG. 5 is a photograph of whole fruit and sectioned fruit of my 'Croft' variety grown in East Wenatchee, Wash., showing high color of skin, yellow flesh, rather small seed (pit), and partial clinging of flesh to the pit, compared with 'Early Redhaven', which shows less color, larger seed (pit), and a similar semi-freestone character. The two whole fruit and two sections of the left side of the picture are of my new variety while the two whole fruit and two sections at the right side of the picture are of the 'Early Redhaven' variety.

The detailed description that follows is based on observations at both Mount Vernon, Wash. (second generation trees) and at East Wenatchee, Wash. (third generation trees). The characteristics were compared with those of the original tree at Tiger Mountain and insofar as have been observed, were the same except for differences in color related to variations in climate between East Wenatchee (averages about ten inches of annual rainfall, colder winter, and hotter summer). The climate in Mount Vernon averages about thirty inches of annual rainfall. Other than fruit color, as of this time no phenotypic differences have been observed at the different locations. Color descriptions (hue/value/chroma) are from the Munsell Book of Color, Kollmorgen Instruments Corp., 405 Little Britain Road, New Winsor, N.Y. 12553.

THE PLANT

Tree

Parentage: Chance seedling of peach tree growing in a cultivated area on Tiger Mountain, Wash.

Tree size: Medium; height 4 m, width 3 m; all trees at present grown on non-dwarfing Lovell rootstock.

Vigor: Moderate.

Chilling requirements: Believed normal for peaches in Washington State. Actual chilling requirements not determined.

Productivity: High, observed as of this time to be approximately 80 pounds (36 kg) per tree at maturity.

Regularity of bearing: Uniform and annual. Requires heavy thinning similar to the 'Redhaven' variety (unpatented) to attain satisfactory size.

Trunk

Size: Medium with medium surface texture becoming rough as tree ages. In East Wenatchee, in July of the year 2000, the trunk size of a fifth leaf tree was 2.5 inches (6 cm). Color: 10 YR 5/2.

Lenticels: Indistinct, same color as bark, like 10YR 5/2.

*Numbers.*—Approximately four per square cm. Numerous.

*Size.*—0.2 mm by 2.0 mm.

Branches

Size and texture: Of medium size, with semi-smooth texture in the immature tree, and medium texture in the mature tree.

Color:

*One year or older wood.*—10 YR 4/8.

*Immature branches.*—7.5 R 2/6.

Lenticels:

*Number.*—Numerous.

*Size.*—0.1 mm by 2.0 mm.

Leaves

Size: Medium to large. Leaves average 15.0 cm in length; 4.5 cm in width.

Form: Lanceolate.

Color:

*Upwardly disposed surface.*—7.5 GY 3/6.

*Downwardly disposed surface.*—5 GY 4/6.

*Vein.*—2.5 GY 7/6.

Marginal form: Finely serrate.

Vein thickness: 1.0 mm to 2.0 mm.

Glandular characteristics: Absent.

Petiole:

*Size.*—Large.

*Length.*—10 mm.

*Thickness.*—2.0 mm.

*Color.*—7.5 GY 3/6.

Stem glands: Absent.

Stipules: Two.

*Length.*—17 mm; non-persistent.

Flowers

Buds:

*Size.*—8 mm by 12 mm.

*Surface texture.*—Slightly pubescent.

Date of bloom: Generally considered mid-season, like 'Early Redhaven', 'Frost', and 'Harbelle' (unpatented) when grown in the same area.

| | | | |
|---|---|---|---|
| Thickness: | 2.0 mm. | | |
| Color: | 7.5 GY 3/6. | | |
| Stem glands: | Absent. | | |
| Stipules: | Two. | | |
| Length: | 17 mm; non-persistent. | | |
| Flowers | | | |
| Buds: | | | |
| Size: | 8 mm by 12 mm. | | |
| Surface Texture: | Slightly pubescent. | | |
| Date of Bloom: | Generally considered mid-season, like 'Early Redhaven', 'Frost', and 'Harbelle' (unpatented) when grown in same area. | | |
| Full Bloom Dates: | 1996 | 1997 | 1998 |
| East Wanatchee | — | 4/19 | 4/5 |
| Mount Vernon | 4/4 | 4/8 | 3/19 |
| Size: | Generally 20 mm to 26 mm. | | |
| Petals: | Petal drop April 15, 1998 (East Wenatchee). | | |
| Number: | Generally 5. | | |
| Color: | 2.5 R 6/6. | | |
| Bloom fragrance: | none. | | |
| Fertility: | Self-fertile. | | |
| Pollen production: | light. | | |
| Fruit | | | |
| Maturity when described: | Ripe for consumer harvesting approximately three days before eating and canning maturity - July 25, 1997 (East Wenatchee), July 22, 1997 (Mount Vernon). Maturity of 'Croft' is approximately the same as that of 'Early Redhaven' in East Wenatchee and approximately the same as that of 'Harbelle' and 'Sentry' in Mount Vernon, approximately twelve days before standard 'Redhaven'. | | |

Size: Generally 20 mm to 26 mm.

Petals: Petal drop Apr. 15, 1998 (East Wenatchee).

*Number.*—Generally 5.

*Color.*—2.5 R 6/6.

Bloom fragrance: None.

Showiness: non-showy, similar to the variety 'Redhaven'.

Fertility: Self-fertile.
Pollen production: Light.

Fruit

Maturity when described: Ripe for consumer harvesting approximately three days before eating and canning maturity—Jul. 25, 1997 (East Wenatchee), Jul. 22, 1997 (Mount Vernon). Maturity of 'Croft' is approximately the same as that of 'Early Redhaven' in East Wenatchee and approximately the same as that of 'Harbelle' and 'Sentry' in Mount Vernon, approximately twelve days before standard 'Redhaven'. Characteristic harvest period is generally from the middle of July to August 1st, varying from the year to year, approximately the same harvest time as the variety 'Early Redhaven.'

Size: Generally, medium; on average about the same as 'Early Redhaven' and 'Redhaven'. Varies somewhat with growing conditions. Characteristic fruit weight is from about 100–200 grams, depending on the degree of thinning.

*Average diameter in the axial plane.*—6.7 cm.
*Average diameter transverse in the suture plane.*—6.3 cm.
*Average diameter transverse and at right angles to the suture plane.*—6.5 cm.

Form:

*Uniformity.*—Globose to slightly oblate.
*Symmetry.*—Symmetrical.

Suture: Generally shallow.
Ventral surface: Generally rounded slightly.
Stem cavity:

*Width.*—20 mm.
*Depth.*—10 mm.
*Length.*—15 mm.
*Shape.*—Acute, funnel shape, elongated in suture plane.

Stem:

*Caliper.*—5 mm.
*Length.*—10 mm.

Apex: Short.
Pistil point: Lacking.
Skin:

*Thickness.*—Thin, less than 1 mm.
*Texture.*—Tender, but easy to peel when fully ripe.
*Blush color.*—7.5 R 4/14. Darker color fruit in East Wenatchee, Wash. climate than in Mount Vernon, Wash.
*Ground color.*—2.5 Y 8/12.
*Tendency to crack.*—None observed.
*Fuzziness.*—Medium, similar to 'Redhaven'.

Flesh:

*Flesh color.*—10 YR 8/14.
*Surface of pit cavity.*—2.5 Y 8/14.
*Color of pit well.*—10 R 4/12.
*Juice production.*—Very juicy.
*Flavor.*—Sweet to subacid; very good.
*Aroma.*—Slight; peachlike.
*Texture.*—Medium.
*Fibers.*—Few, but not objectionable.
*Ripening.*—Tends to soften along suture and apex slightly before the sides of the fruit.
*Eating quality.*—Very good. Superior to 'Early Redhaven' and 'Frost'; comparable to 'Redhaven'.

Stone:

*Attachment.*—Semi-freestone.
*Fibers.*—Numbers: Few. Length: 6–7 mm.
*Size.*—Length: 31 mm. Width: 20 mm. Thickness: 15 mm.
*Form.*—Generally ovoid.
*Apex — Shape.*—Short, pointed.
*Color — Dry.*—5 R 8/2.
*Base — Shape.*—Straight.
*Sides.*—Generally equal.
*Ridges.*—Semi-sharp.
*Tendency to split.*—Up to thirty percent in Western Washington (Mount Vernon); 10–20% in East Wenatchee (warmer climate).

Use: Local market and home garden; commercial potential not assessed.
Keeping quality: Medium, similar to that of 'Redhaven'.
Resistance to disease: Highly resistant, but not totally immune, to leaf curl (*Taphrina deformans* (Berk.)); susceptibility to other peach diseases, e.g. brown rot, comparable to 'Redhaven' and 'Frost'.
Shipping and handling qualities: Unknown, but from early evaluations, comparable to 'Redhaven'. Probably inferior to newer cultivars bred for commercial shipping.

Although the new variety of peach possesses the described characteristics noted above when grown at Tiger Mountain (Issaquah), Mount Vernon, and East Wenatchee, it is to be understood that variations in characteristics as a result of different growing conditions, irrigation, fertilization, pruning, pest control, and the like are to be expected.

Having thus described and illustrated my new variety of peach tree, what I claim as new is:

1. A new and distinct variety of peach tree substantially as illustrated and described, which is highly resistant to leaf curl disease (*Taphrina deformans* Berk.); has yellow flesh, ripens similar to 'Early Redhaven', is semi-freestone when fully ripe; and has a fruit quality like that of 'Early Redhaven' and 'Redhaven'.

* * * * *

UNITED STATES PATENT AND TRADEMARK OFFICE

CERTIFICATE OF CORRECTION

PATENT NO. : PP 11,769 P2
DATED : February 6, 2001
INVENTOR(S) : Margaret J. Proud It is certified that error appears in the above-identified patent and that said Letters Patent is hereby corrected as shown below:

Title page,
Item [57], ABSTRACT,
Line 7, change "(Berk.)." to -- (Berk.) Tul. --

Column 4,
Lines 32-60, between the two black bars, please delete. Replace with:

| -- | Full Boom Dates: | 1996 | 1997 | 1998 |
|---|---|---|---|---|
| | East Wenatchee | – | 4/19 | 4/5 |
| | Mount Vernon | 4/4 | 4/8 | 3/19 -- |

Signed and Sealed this

Nineteenth Day of November, 2002

*Attest:*

*Attesting Officer*

JAMES E. ROGAN
*Director of the United States Patent and Trademark Office*